United States Patent [19]

Lapidus

[11] 4,195,972

[45] Apr. 1, 1980

[54] AQUEOUS-BASED HAIR DYEING COMPOSITION CONTAINING A SOLUBLE BISMUTH SALT AND A REDUCING COMPOUND

[75] Inventor: Herbert Lapidus, Ridgefield, Conn.

[73] Assignee: Combe Incorporated, White Plains, N.Y.

[21] Appl. No.: 953,127

[22] Filed: Oct. 20, 1978

[51] Int. Cl.$^2$ .............................................. A61K 7/12
[52] U.S. Cl. ............................................ 8/10.1; 8/10
[58] Field of Search ............................. 8/10.1, 10

[56] References Cited

U.S. PATENT DOCUMENTS

| | | | |
|---|---|---|---|
| 1,937,365 | 11/1933 | Stoddard et al. | 8/10.1 |
| 2,733,186 | 1/1956 | de Brye | 8/10.2 |
| 2,763,269 | 9/1956 | Beste | 8/10.1 |
| 3,202,579 | 8/1965 | Berth et al. | 8/10.2 |
| 3,415,608 | 12/1968 | Tucker | 8/10.2 |
| 3,954,393 | 5/1976 | Lapidus | 8/10.1 |
| 3,961,879 | 6/1976 | Bugaut et al. | 8/10.1 |
| 3,986,825 | 10/1976 | Sokol | 8/10.1 |

*Primary Examiner*—Allen J. Robinson
*Attorney, Agent, or Firm*—Bryan & Bollo

[57] ABSTRACT

A hair dyeing composition comprising a metal salt and a sulfur-containing reducing compound is described. In the composition, the metal salt is a water-soluble bismuth salt of an alpha-hydroxy, mono-carboxylic acid.

11 Claims, No Drawings

AQUEOUS-BASED HAIR DYEING COMPOSITION CONTAINING A SOLUBLE BISMUTH SALT AND A REDUCING COMPOUND

BACKGROUND OF THE INVENTION

This invention pertains to a composition designed for use in dyeing human hair. While various forms of such dyeing compositions are known, a category of particular importance involves those containing a metal salt and a sulfur-containing reducing compound in an aqueous vehicle. Depending, in particular, upon the nature of the metal salt, these compositions may be employed to impart a variety of colors to human hair.

A class of metal salts which has proven particularly desirable is salts containing bismuth. Unfortunately, however, bismuth salts which are useful in such hair dyeing compositions have not proven readily susceptible to formulation.

This lack of success in formulating bismuth-containing hair dyeing compositions is partly a function of the limited number of known and active bismuth compounds which are soluble in conventional hair dyeing vehicles, particularly water. In addition, it is attributed to the low stability usually evidenced by bismuth salts in the presence of sulfur-containing reducing compounds. As a consequence, the use of bismuth salts for dyeing hair has been greatly limited.

In U.S. Pat. Nos. 1,937,365 and 2,719,104, there are described dyeing compositions utilizing inorganic salts of bismuth. These patents, however, require a number of different auxillary agents and indicated wide differences in coloration—viz. blond, red and brown—dependent upon these ingredients. Also, they are generally very unstable and so difficult to employ.

In U.S. Pat. No. 3,954,393 of Lapidus, there is disclosed another means by which useful hair dyeing compositions containing a bismuth salt may be obtained. There, an aqueous formulation including bismuth citrate solublized by triethanolamine is described. That formulation yields various hair shades of brown. The scope of that invention is, however, limited. Consequently, many bismuth compounds remain unused.

DESCRIPTION OF THE INVENTION

The present invention is directed to the provision of a hair dyeing composition which, upon use, produces desirable color shades when applied to human hair. This composition contains a metal salt and a sulfur-containing reducing compound in an aqueous vehicle. In this composition, the metal salt is a water-soluble bismuth salt of an alpha-hydroxy, mono-carboxylic acid.

It has been discovered that the present water-soluble bismuth salts of alpha-hydroxy, mono-carboxylic acids are both active (in combination with a sulfur-containing reducing compound) to induce desirable coloring of hair and are natively water-soluble. Moreover, these salts are quite stable in the presence of sulfur-containing reducing compounds until applied to the hair. As a consequence, a hair dyeing composition which is simply and readily prepared may be formulated.

In the present compositions, the anion of the present bismuth salts is obtained from alpha-hydroxy, mono-carboxylic acids. Exemplary of such acids are hydroxy acetic acid, lactic acid, glyceric acid, and glutonic acid. As these representative examples indicate, the composition of the present acids may vary greatly, so long as they maintain an alpha-hydroxy, carboxylic moiety.

In general, however, the acids contain between 2 and 20, preferably 2 to 10 and most preferably 2 and 4 carbons.

Other than the alpha-hydroxy, carboxylic moiety, it is also generally preferred that the remainder of the acid be composed essentially of a hydrocarbon, normally a saturated hydrocarbon such as an alkyl group. Alternatively preferred are the alcohol derivatives of these hydrocarbons such as a hydroxy substituted alkyl group, so as to result in a poly-hydroxylated acid. In addition to the foregoing, however, various substituents, including halide, keto, aldehydic and other functional groups may be present, so long as the resultant bismuth salt remains water-soluble.

The amount of bismuth salt employed in the present compositions may vary generally within conventional limits. Customarily, however, this salt is present in an amount of up to about 5%, preferably 0.1 to 1.0% and most preferably 0.25 to 0.75% by total weight of the composition. This degree of dilution permits ready control over the extent of hair dyeing.

To produce a hair dyeing composition in accordance with the present invention, the bismuth salt of an alpha-hydroxy, mono-carboxylic acid may initially simply be dissolved in all, or a portion, of the aqueous vehicle to be utilized. Alternatively, this salt may be produced in situ by reaction of a different bismuth salt (normally a water-insoluble bismuth salt, such as bismuth nitrate or bismuth sub-nitrate) with a suitable alpha-hydroxy, mono-carboxylic acid (usually an excess thereof, ranging between about 1 and 4 mole per mole of bismuth).

The sulfur-containing reducing compound utilized in accordance with the present invention may be selected from among any of the conventional such agents for hair dyeing compositions. Exemplary are thiourea and thioglycolates. In a preferred embodiment in accordance with the present invention, however, the reducing compound is either sulfur or thiosulfate (normally the ammonium or alkali metal salts thereof.) Sulfur is generally employed in its finely divided, suspendable form. Thiosulfates, on the other hand, are water-soluble and hence readily employed in dissolved form in the present compositions.

The reducing compound of the present invention may be utilized in any effective amount as, for example, known for other metallic salt dyes or as is readily determined. These compounds are, however, customarily employed in a mole ratio of from about 0.5:1 to 10:1, most preferably 1:1 to 3:1, based upon the bismuth present.

The vehicle for the present dye system of a bismuth salt and a reducing compound comprises water and normally is at least 30%, preferably between 60 and 100%, water by total weight. The remaining non-aqueous portion, if any, of the vehicle may be any liquid miscible therewith.

The amount of vehicle (or aqueous solvent) of the present invention will vary in conventional manner. It is preferred, however, that such vehicle constitute between about 50 and 90, most preferably 75 and 90% by total composition weight. This ensures a manageable dyeing strength for the present compositions.

In preparing the hair dyeing compositions of the present invention, it is generally most convenient first to prepare separate aqueous portions of the soluble bismuth salt and of the reducing compound. These two portions may then be mixed together to produce the present composition. The resultant composition remains quite stable, without any substantial undesirable precipitation. When applied to the hair, it appears that a form of the chemical reaction influenced by the keratinaceous nature of hair and/or various other hair components such as oil, takes place. This reaction is manifested, in part, by the darkening or dyeing of the hair to the desired shade.

Of major importance to the present invention is the foregoing fact that it is only upon contact with the hair that substantial reaction between the bismuth salt and the reducing compound is commenced. Therefore, the compositions remain stable until activated by the hair they are intended to dye.

While soluble bismuth salt of an alpha-hydroxy, mono-carboxylic acid, a reducing component and an aqueous vehicle are the essential components in the composition of this invention, it is understood that various additional ingredients may be present. These include, for example, such conventional additives as a wetting agent which will facilitate the dispersion of, for example, sulfur. Particularly preferred as a wetting agent are ethylene oxide-alcohol condensation products such as Triton X-100 (a Rohm & Haas condensation product of iso octyl phenyl polyethoxy ethanol with between 9 and 10 moles of ethylene oxide). Similarly, a humectant such as glycerin may be employed to stabilize the reaction on the hair. Grooming agents, such as propylene glycol, mineral oil, fatty acid esters and the like, may also be present. Where water immiscible these agents are normally emulsified with the aqueous dye system to produce a lotion form of product. Further, perfumes and the like may be incorporated into the composition.

The hair dyeing compositions of this invention normally exhibit a pH of between about 3.0 and 10.5, preferably 5.0 and 10. These have been found to ensure stability of the composition while permitting application to the hair without adverse affect.

In addition to the foregoing, conventional additives for hair dyeing compositions, a particularly preferred additive is N-acetyl ethanolamine (often referred to as Acetamide MEA). This compound, particularly in an amount of from about 1 to 25%, most preferably 10 to 15% by total weight of composition has been discovered to be a highly desirable dyeing enhancer. Its use in dye systems in general is described in detail in U.S. application Ser. No. 951,998 of Herbert Lapidus entitled DYEING COMPOSITIONS FOR FIBROUS MATERIALS, filed currently herewith, the disclosure of which is incorporated herein by reference. N-acetyl ethanolamine will greatly accelerate and deepen the coloring effect of the present composition. In addition, it has been found to render the resultant color more resistent to fading or removal from the hair.

In order to more clearly describe this invention, several examples of compositions of the present invention are described below. It should be understood, however, that these examples are provided solely for illustration and are not intended to limit the scope of the invention.

EXAMPLE I

| Ingredients | Percent (by total weight) |
| --- | --- |
| Bismuth sub nitrate | 0.75% |
| Lactic Acid (85%) | 4.00 |
| Glycerin | 10.00 |
| Sulfur precipitate | 1.00 |
| Triton X-100 | 0.10 |
| Water | 84.15 |

A hair dyeing composition having the above-indicated formula was prepared as follows:

(a) The sulfur and Triton X-100 were added to an aliquot of water and ground to disperse the sulfur in a fine, semi-colloidal form;

(b) The bismuth sub nitrate, glycerin and lactic acid were placed in a kettle and heated at 70° C. until clear. During heating, the lactic acid displaced the nitrate to form bismuth lactate;

(c) The clear solution resultant from Step (b) was cooled by the addition of cold water, while mixing, and then the product of Step (a) was added to produce the composition.

To test the above composition, swatches of bleached hair were dunked into the hair dyeing composition, removed, shaken to remove excess composition, and then permitted to dry overnight at room temperature. After drying, the hair was observed to have changed from its initial blondish color to a shade of brown. Repeated daily treatment over three weeks yielded an increasing deeper or darkened shade of brown.

EXAMPLE II

| Ingredients | Percent (by total weight) |
| --- | --- |
| Bismuth citrate | 0.50% |
| Hydroxy acetic acid (70%) | 2.00 |
| Triethanolamine | 1.50 |
| Glycerin | 10.00 |
| Sulfur precipitate | 1.00 |
| Triton X-100 | 0.10 |
| Water | 84.90 |

A hair dyeing composition having the foregoing indicated ingredients was prepared, using the procedure set forth in Example I. This composition again evidenced the ability to dye bleached hair to a dark shade of brown.

It is claimed:

1. In a hair dyeing composition comprising a metal salt and a sulfur-containing reducing compound in an aqueous vehicle, the improvement wherein said metal salt comprises a water-soluble bismuth salt of an alpha-hydroxy, mono-carboxylic acid.

2. The composition of claim 1, wherein the alpha-hydroxy carboxylic acid is hydroxy acetic acid.

3. The composition of claim 1, wherein the alpha-hydroxy carboxylic acid is lactic acid.

4. The composition of claim 1, wherein the reducing compound is sulfur.

5. The composition of claim 1, wherein the reducing compound is an alkali metal thiosulfate.

6. The composition of claim 1, wherein the bismuth salt is present in an effective amount of up to about 5% by total composition weight.

7. The composition of claim 6, wherein the reducing compound is present in a mole ratio of from about 0.5:1 to 10:1 based on bismuth.

8. The composition of claim 1, wherein the anion of the bismuth salt is a poly-hydroxy, mono-carboxylic acid.

9. The composition of claim 1, wherein the anion of the bismuth salt is an acid having between 2 and 20 carbons.

10. The composition of claim 1, wherein the composition additionally contains N-acetyl ethanolamine.

11. The composition of claim 1, wherein the pH of the composition is between about 3.0 and 10.5.

* * * * *